(12) United States Patent
Itoh

(10) Patent No.: US 9,261,449 B2
(45) Date of Patent: Feb. 16, 2016

(54) TEST PREPROCESSING APPARATUS, TEST PREPROCESSING METHOD, AND SPECIMEN PROCESSING APPARATUS

(75) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 582 days.

(21) Appl. No.: 13/615,941

(22) Filed: Sep. 14, 2012

(65) Prior Publication Data

US 2013/0076882 A1      Mar. 28, 2013

(30) Foreign Application Priority Data

Sep. 28, 2011  (JP) ................................. 2011-213294

(51) Int. Cl.
| G01N 15/04 | (2006.01) |
| G01N 15/05 | (2006.01) |
| G01N 33/49 | (2006.01) |
| G01N 21/25 | (2006.01) |
| G01N 35/10 | (2006.01) |

(52) U.S. Cl.
CPC ................ *G01N 15/05* (2013.01); *G01N 21/25* (2013.01); *G01N 2035/1025* (2013.01)

(58) Field of Classification Search
CPC ..................................................... G01N 21/00
USPC ............................ 356/39; 422/82.09; 348/649
See application file for complete search history.

(56) References Cited

U.S. PATENT DOCUMENTS

| 4,263,512 A * | 4/1981 | Sagusa et al. ................. 250/373 |
| 5,763,265 A * | 6/1998 | Itsuzaki et al. ............. 435/288.7 |
| 2007/0222973 A1* | 9/2007 | Hoshiko .............. G01N 21/253 356/39 |
| 2010/0303331 A1 | 12/2010 | Itoh |
| 2011/0045521 A1 | 2/2011 | Itoh |
| 2012/0140230 A1 | 6/2012 | Miller |

FOREIGN PATENT DOCUMENTS

| CN | 1560599 A | 1/2005 |
| CN | 101010579 A | 8/2007 |
| CN | 101151534 A | 3/2008 |
| CN | 101726612 A | 6/2010 |
| CN | 101907559 A | 12/2010 |
| CN | 101995342 A | 3/2011 |
| CN | 102043061 A | 5/2011 |
| EP | 1 845 363 A2 | 10/2007 |
| EP | 2 287 622 A1 | 2/2011 |
| JP | 2000-227399 | 8/2000 |
| JP | 2001-165752 | 6/2001 |
| JP | 2006-011531 | 2/2006 |

(Continued)

OTHER PUBLICATIONS

CN Office Action and Search Report and English translation dated Jun. 20, 2014 in CN 2012103663248.

(Continued)

*Primary Examiner* — Dave Czekaj
*Assistant Examiner* — Alison Slater
(74) *Attorney, Agent, or Firm* — Nixon & Vanderhye P.C.

(57) ABSTRACT

According to an embodiment, a test preprocessing method includes, detecting a brightness of a specimen based on image of the specimen acquired by capturing the specimen before test processing of the specimen, and detecting a chylous state of the specimen based on the brightness, and detecting a hue of the specimen based on the image, and detecting a hemolytic state of the specimen based on the hue.

8 Claims, 12 Drawing Sheets

(56) References Cited

FOREIGN PATENT DOCUMENTS

| | | | |
|---|---|---|---|
| JP | 2008-76185 | 4/2008 | |
| JP | 4452277 | 2/2010 | |
| JP | 2010-281604 | 12/2010 | |
| KR | 10-2009-0047860 | 5/2009 | |
| KR | 10-2010-0130163 | 12/2010 | |
| TW | 201109663 A1 | 3/2011 | |
| TW | 201122454 A1 | 7/2011 | |
| WO | WO 2006/011531 A1 | 2/2006 | |
| WO | WO 2011/019576 A1 | 2/2011 | |
| WO | WO 2011019576 A1 * | 2/2011 | ............ G01N 21/00 |

OTHER PUBLICATIONS

Extended European Search Report in EP 12 00 6698 dated Mar. 11, 2013.
Letter from Gramm, Lins & Partner forwarding Search Report dated Mar. 14, 2013.
Korean Action and English translation in KR 2012-0107396 mailed Oct. 31, 2013.
Office Action and English translation in JP 2011-213294 mailed Sep. 10, 2013.
Taiwanese Office Action issued in Patent Application No. 101135290 dated Dec. 2, 2014 (w/ partial translation).

* cited by examiner

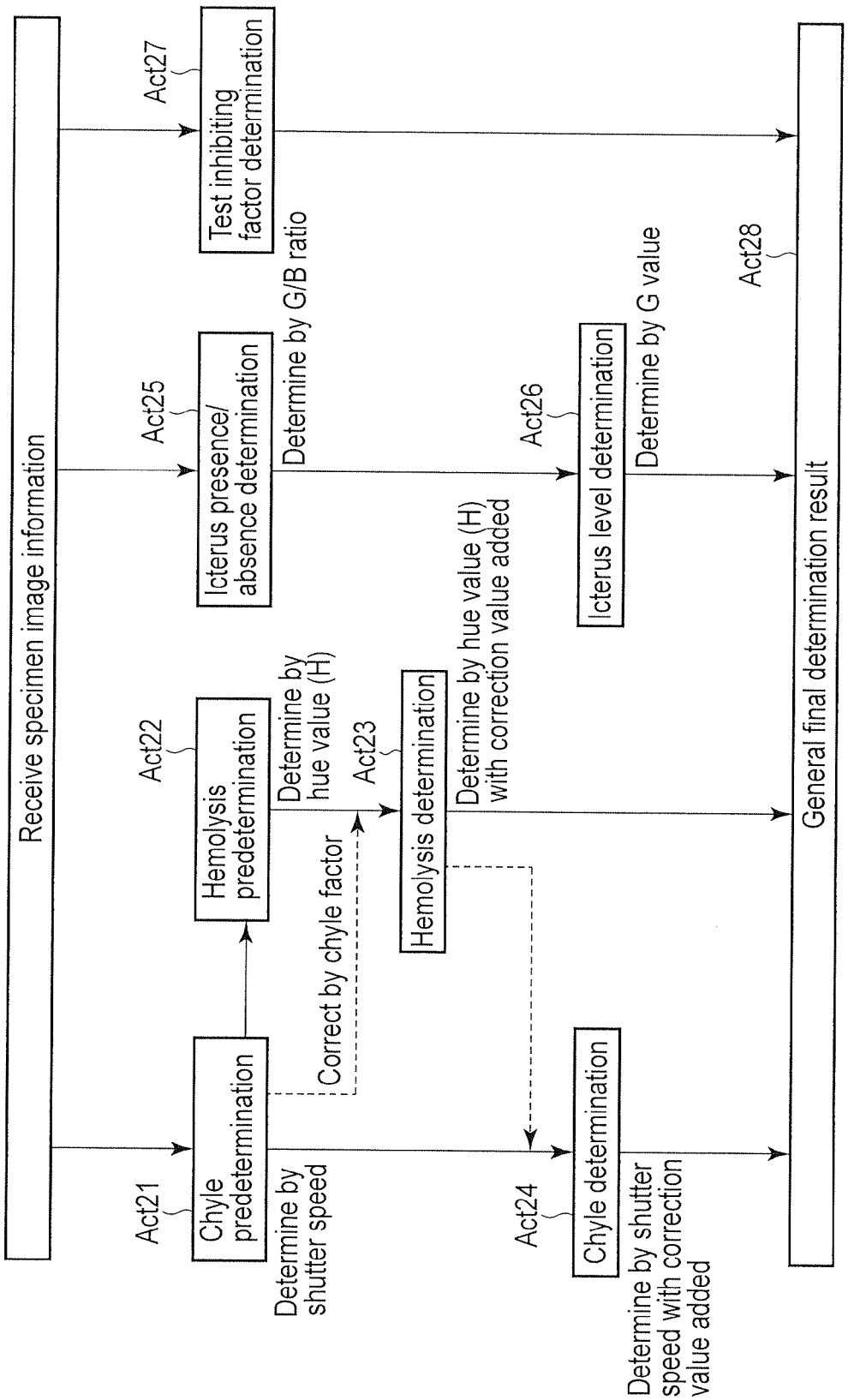
F I G. 5

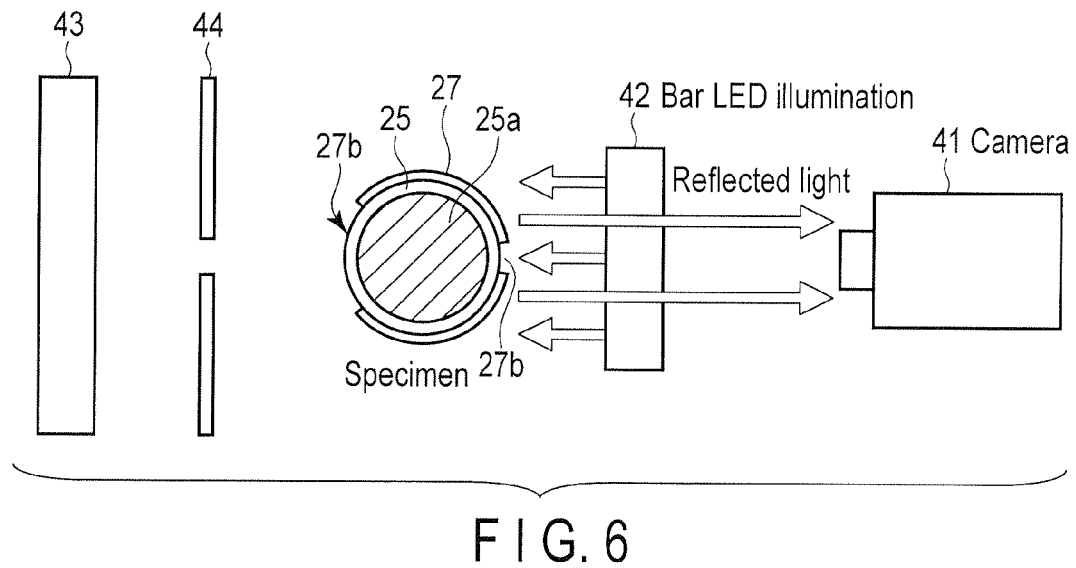
F I G. 6
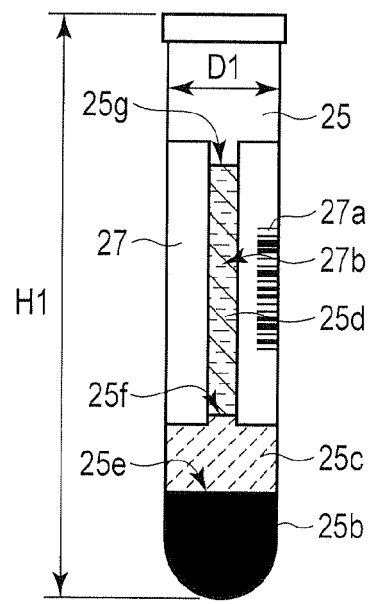
F I G. 7

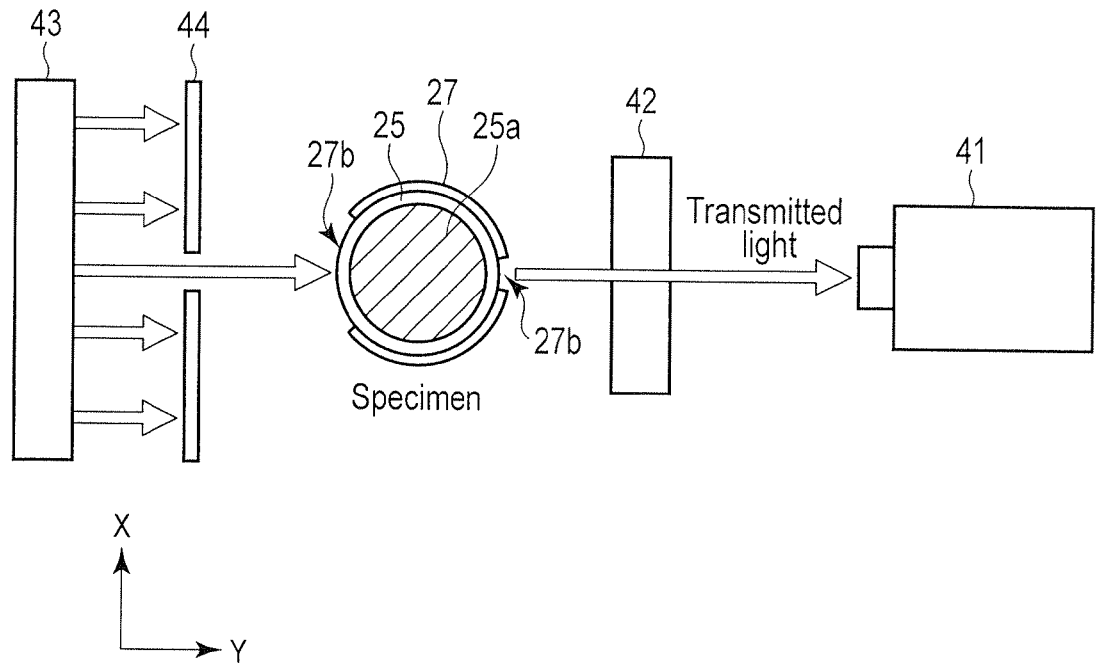
F I G. 8
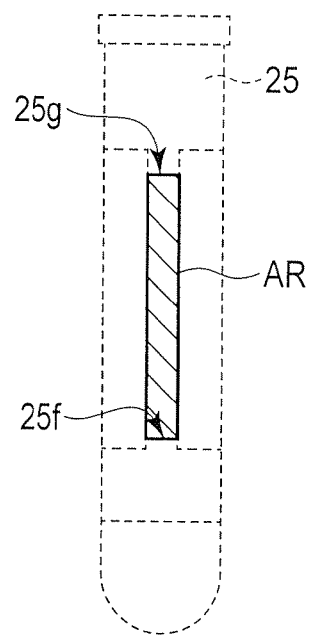
F I G. 12

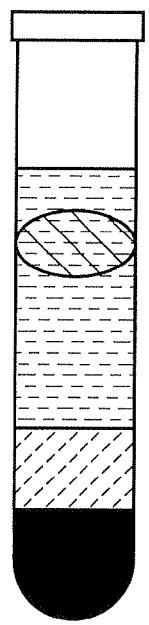
F I G. 13A
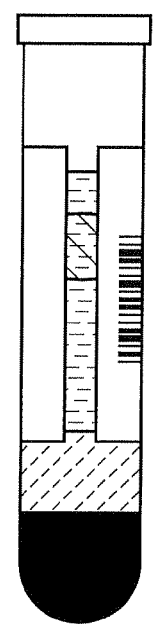
F I G. 13B
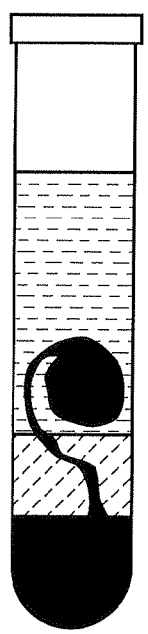
F I G. 14A
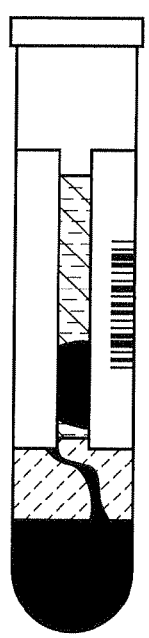
F I G. 14B

TEST PREPROCESSING APPARATUS, TEST PREPROCESSING METHOD, AND SPECIMEN PROCESSING APPARATUS

CROSS-REFERENCE TO RELATED APPLICATIONS

This application is based upon and claims the benefit of priority from prior Japanese Patent Application No. 2011-213294, filed Sep. 28, 2011, the entire contents of which are incorporated herein by reference.

BACKGROUND OF THE INVENTION

1. Field of the Invention Embodiments described herein relate generally to a test preprocessing apparatus, a test preprocessing method, and a specimen processing apparatus.

2. Description of the Related Art

In processing for various kinds of blood tests such as biochemical analysis, the state of the specimen or the specimen container may affect the test result (for example, Jpn. Pat. Appln. KOKAI Publication No. 2008-76185). For example, if blood serum is in a chylous, hemolytic, or icteric state, contains an impurity such as fibrin, or has defective blood clotting, the state affects the test result later or makes it impossible to conduct the test. Hence, in general, the operator visually confirms the color of the specimen to detect its state, or an analysis apparatus is used to test a specimen reacted with a reagent.

Detecting a test inhibiting factor before a test enables to prevent waste of reagents or processing for the test. However, there is a demand for more accurate and quick processing. In particular, sequentially detecting a plurality of inhibitors requires a long time. In addition, since different inhibitors may affect each other, accurate detection is difficult.

BRIEF SUMMARY OF THE INVENTION

According to an embodiment, a test preprocessing method comprises, detecting a brightness of a specimen based on image of the specimen acquired by capturing the specimen before test processing of the specimen, and detecting a chylous state of the specimen based on the brightness, and detecting a hue of the specimen based on the image, and detecting a hemolytic state of the specimen based on the hue.

BRIEF DESCRIPTION OF THE SEVERAL VIEWS OF THE DRAWING

FIG. 5 is a flowchart showing steps in test inhibiting factor detection processing of the test preprocessing method;

FIG. 6 is an explanatory view showing first image capture processing of the test inhibiting factor detection step;

FIG. 7 is an explanatory view showing bar code reading processing and a specimen size detection step in the test inhibiting factor detection step;

FIG. 8 is an explanatory view showing second image capture processing and third image capture processing of the test inhibiting factor detection step;

FIG. 12 is an explanatory view showing region specification processing of the test inhibiting factor detection step;

FIGS. 13A and 13B are explanatory views showing a specimen with a fibrin inclusion in the test inhibiting factor detection step;

FIGS. 14A and 14B are explanatory views showing a specimen with defective blood clotting in the test inhibiting factor detection step;

DETAILED DESCRIPTION OF THE INVENTION

[First Embodiment]

Figure 1:
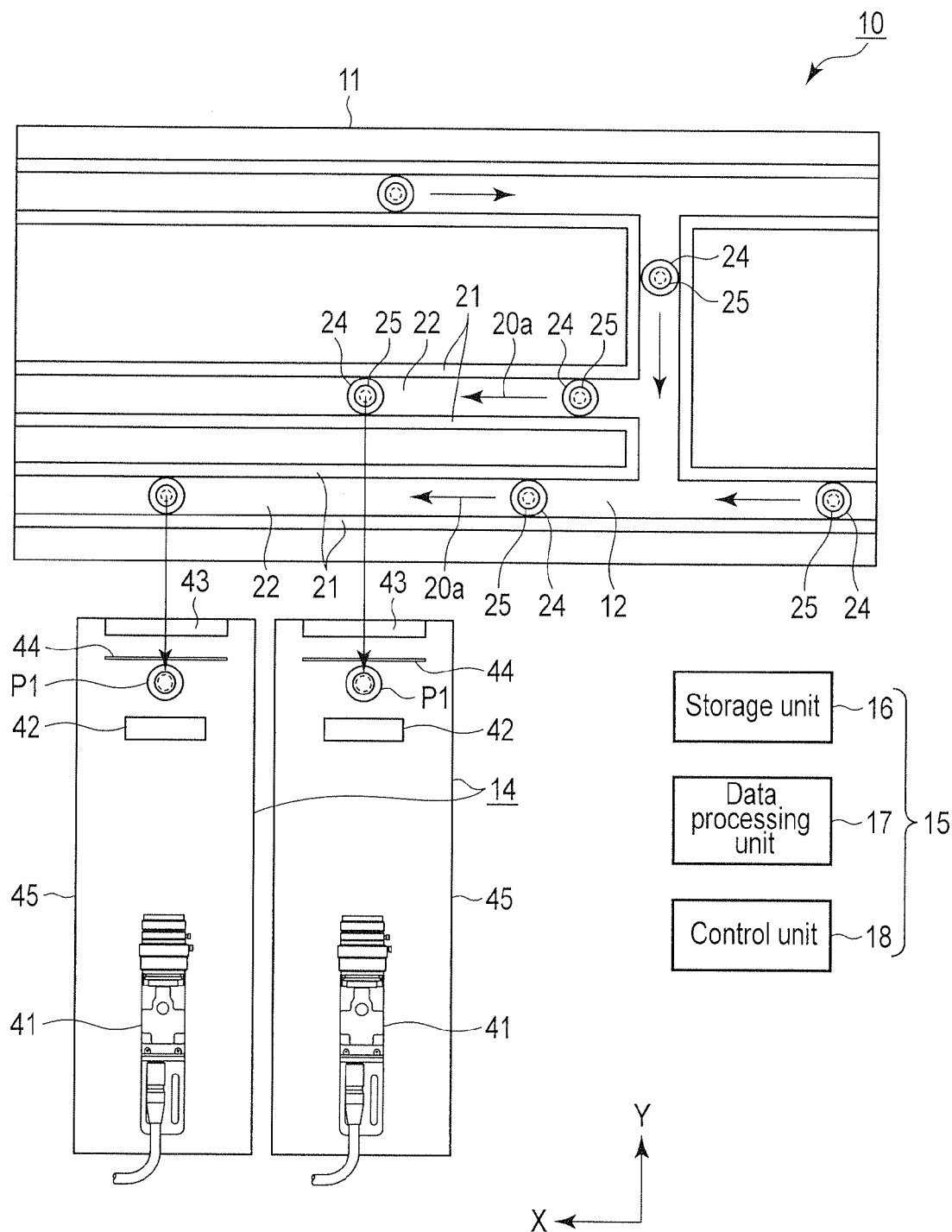
FIG. 1 is a plan view showing the arrangement of a test preprocessing apparatus according to the first embodiment of the present invention.

A test preprocessing apparatus 10 and a test preprocessing method according to an embodiment of the present invention will now be described FIGS. 1, 2, 3, 4, 5, 6, 7, 8, 9, 10, 11, 12, 13, and 14. Note that these drawings enlarge, reduce, or omit the components as needed. Arrows X, Y, and Z in the drawings indicate three directions perpendicular to each other.

Figure 2:
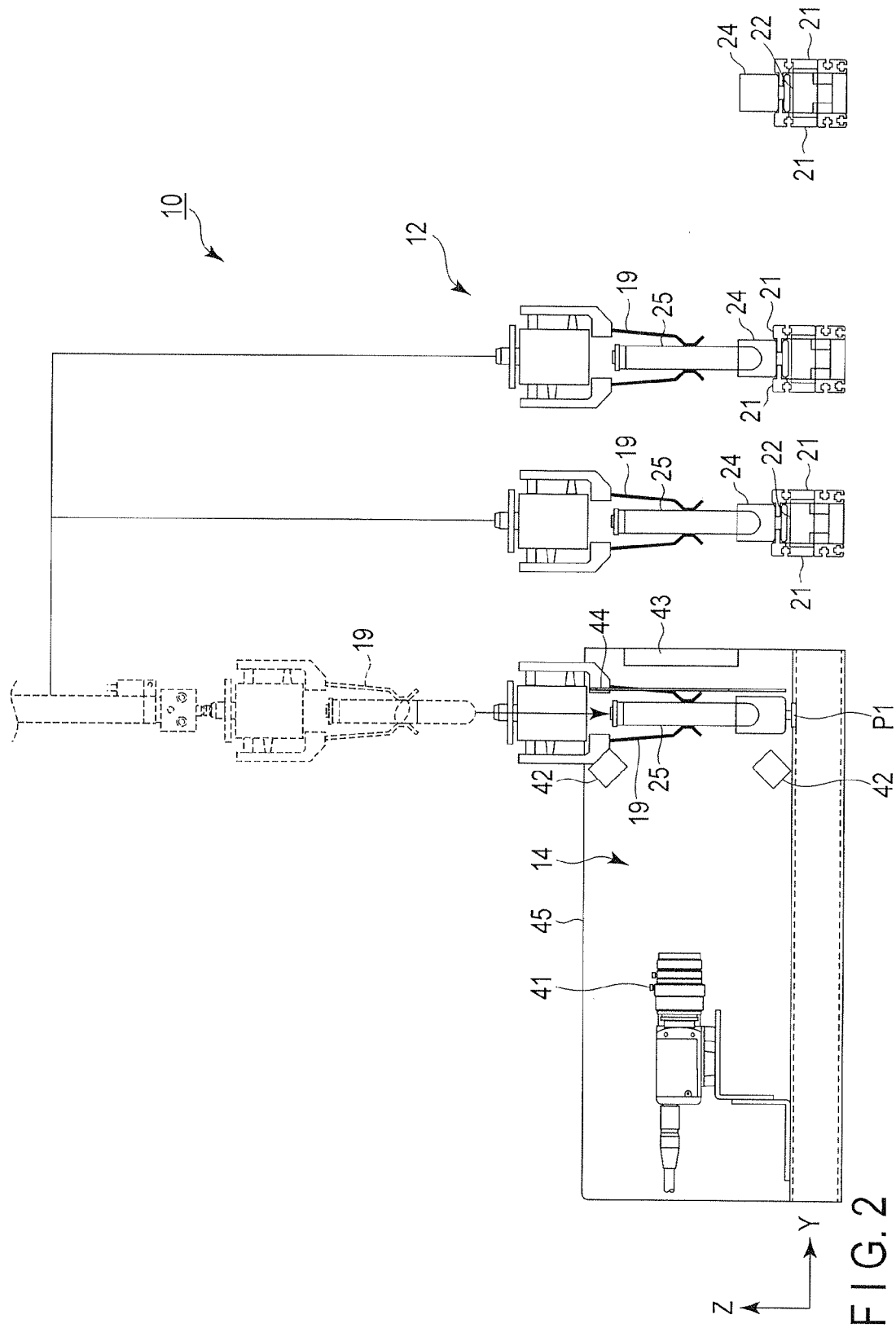
FIG. 2 is a side view showing the arrangement of the test preprocessing apparatus.

FIGS. 1 and 2 are explanatory views schematically showing the test preprocessing apparatus 10 according to this embodiment. The test preprocessing apparatus 10 detects the state of a specimen in advance before various kinds of processing for a test such as biochemical analysis of the specimen and is used as one of preprocessing apparatuses of, for example, an analysis apparatus. In this embodiment, as the test inhibiting factors, test inhibiting factor present states such as the presence of a fibrin inclusion and defective blood clotting are detected as well as a chylous, hemolytic, and icteric states.

The test preprocessing apparatus 10 includes an apparatus main body 11, a conveyance unit 12 that conveys a test tube 25 (specimen container) along a predetermined conveyance path 20a, an image acquisition unit 14 that acquires image information (image) by capturing the specimen, and a test inhibiting factor detection unit 15 (a specimen state detection unit) that performs test inhibiting factor detection processing based on various kinds of images acquired by the image acquisition unit 14.

As shown in FIGS. 1 and 2, the conveyance unit 12 is a conveyor-type holder conveyance mechanism provided above the apparatus main body 11. The conveyance unit 12 includes a pair of guide rails 21 installed in a predetermined width along the conveyance path 20a extending in the X-axis direction in FIG. 1, a conveyor belt 22 arranged between the guide rails 21 along the conveyance path 20a, and a driving unit such as a conveyance roller that rotationally drives the conveyor belt 22 from the lower side to feed it.

A holder 24 for holding the test tube 25 engages between the pair of guide rails 21 so as to be supported upright and conveyed as the conveyor belt 22 moves. The conveyance unit 12 also includes a transfer mechanism 19 such as a robot arm.

The test tube 25 serving as a specimen container for storing a specimen 25a is held by the holder 24 and conveyed in an upright state along the conveyance path 20a. Processing apparatuses provided along the conveyance path 20a perform various kinds of processing for the test tube 25 or the specimen 25a. The test tube 25 is transferred from the conveyance path 20a to an image capture point P1 in a chamber 45 by the transfer mechanism 19 while remaining upright, and undergoes image capture processing (photographing processing) in the chamber 45. The test tube 25 that has undergone the image capture is returned to the conveyance path 20a by the transfer mechanism 19 and fed to the downstream side.

Figure 3:
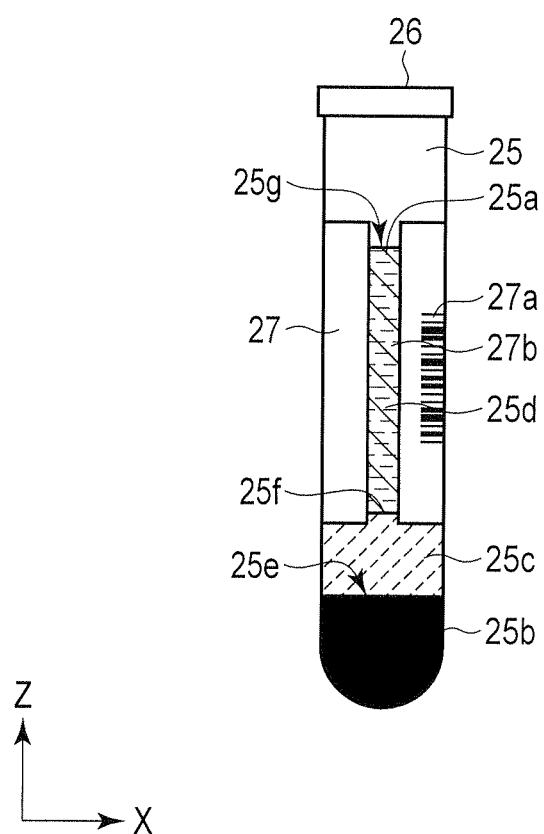
FIG. 3 is an explanatory view showing a specimen container and a specimen according to the embodiment.

As shown in FIG. 3, the test tube 25 is made of transparent glass or the like and formed into a cylindrical shape having a cylindrical space to store the specimen. For example, a label 27 is adhered to the outer peripheral surface of the test tube 25. The label 27 shows a bar code 27a that serves as an identification information indicator representing various kinds of information such as identification information of the specimen 25a.

The specimen 25a in the test tube 25 is separated into a blood clot layer 25b, a separating medium (silicone) layer 25c, and a blood serum layer 25d, and the three layers are arranged sequentially from the lower side in the order named. A first interface 25e is formed between the blood clot layer 25b and the separating medium layer 25c. A second interface 25f is formed between the separating medium layer 25c and the blood serum layer 25d. A specimen liquid surface 25g is formed on the blood serum layer 25d.

The label 27 is provided with a pair of exposed portions 27b on the front and rear sides (only one exposed portion is illustrated in FIG. 3), each of which has a predetermined width and can pass light when being irradiated with backlight at the time of backlight image capture.

Note that as a condition for enabling image information acquisition by passing light upon backlight image capture, a region of the blood serum layer 25d, which has a desired width (for example, 2 mm or more), needs to be exposed to the peripheral surface of the test tube 25 between a pair of predetermined portions on the front and rear sides so that the light can pass between an image capture unit 41 and a backlight 43. In this case, the exposed portions 27b are formed by peeling off a pair of predetermined regions of the label 27 in advance by another preprocessing. However, label peeling processing of peeling off the label 27 at a necessary portion in advance may be performed by another apparatus, as will be described later.

As shown in FIGS. 1 and 2, the image acquisition unit 14 comprises the image capture unit 41 (image detection means) that captures the side of the test tube 25 to acquire the image information of the specimen, a front light 42 that irradiates the test tube with light from the front surface side, the backlight 43 that irradiates the test tube with light from the rear surface side, a slit plate 44 provided between the test tube and the backlight 43, and the chamber 45 that accommodates these components.

The front light 42 is formed from a pair of white LEDs arranged on the upper and lower sides of the image capture unit 41, and irradiates the test tube 25 from the side image capture front surface direction (Y direction) of the test tube 25. The backlight 43 is formed from, for example, a white LED, and irradiates the test tube 25 from the side image capture rear surface direction of the test tube 25. The slit plate 44 has a slit 44a in a region where the backlight illumination needs to pass through and shields the light in regions other than the region so as to regulate light transmission and prevent light diffusion at the time of backlight image capture. Note that at the image capture point P1, the test tube is set such that the exposed portions 27b are located on the image capture front and rear surfaces.

The image capture unit 41 (image detection means) is formed from an image sensor such as a CCD and provided on a side of an image capture point P. The image capture unit 41 is configured to be able to change the shutter speed. The image capture unit 41 can adjust the brightness by repetitively performing image capture processing while changing the shutter speed. The higher the shutter speed is, the shorter the shutter open time is, and the smaller the light amount is. On the other hand, the lower the shutter speed is, the longer the shutter open time is, and the larger the light amount is. The image capture unit 41 captures the side surface of the specimen 25a from a side of the test tube 25 held upright at the image capture point P1, thereby acquiring image information. The acquired image information is recorded in a storage unit 16 and sent to a data processing unit 17.

The chamber 45 is provided on, for example, a side of the conveyance path 20a. The image capture point P1 is provided at a predetermined position on the inner bottom surface of the chamber 45, and the holder 24 is installed there. The upper surface of the chamber 45 is provided with a lid that can open/close when putting in and taking out the test tube 25.

The image acquisition unit 14 operates under the control of a control unit 18 to perform backlight image capture of performing image capture while causing the backlight 43 to emit light and front light image capture of performing image capture while causing the front light 42 to emit light at predetermined timings.

At the time of front light image capture, the image capture unit 41 irradiates the front surface of the test tube 25 with light and captures the image from the front surface side, thereby acquiring the image information of the specimen 25a in the transparent test tube 25. At the time of backlight image capture, the image capture unit 41 guides the light through the exposed portions 27b on the front and rear sides and captures the image from a side of the front surface, thereby acquiring the image information of the internal specimen 25a.

The test inhibiting factor detection unit 15 comprises the storage unit 16 (storage means) that stores various kinds of data including image information, the data processing unit 17 that performs data processing such as calculation and determination including image processing based on the various kinds of data, and the control unit 18 (control means) that controls the operations of the units in addition to the above-described image acquisition unit 14.

Figure 4:
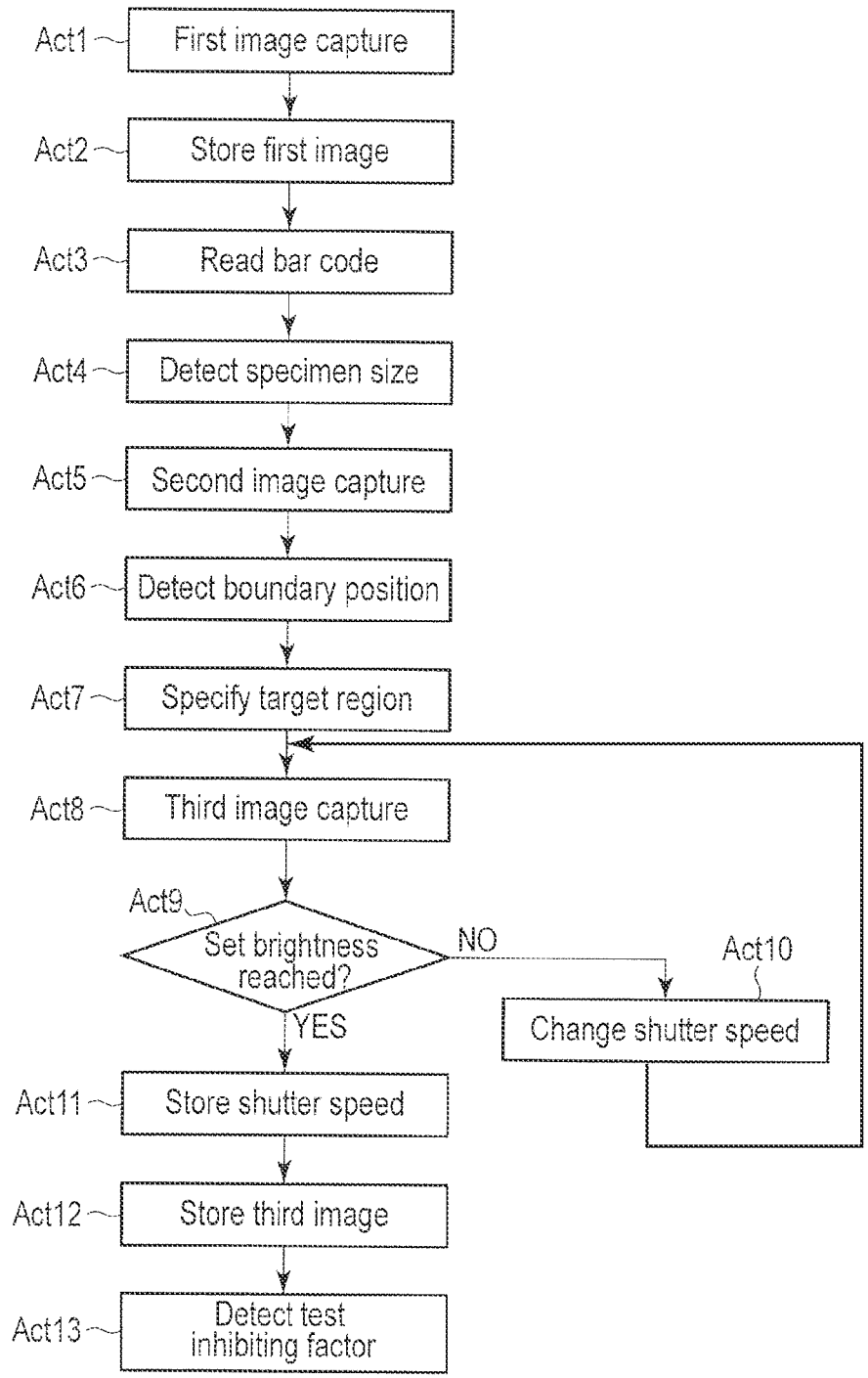
FIG. 4 is a flowchart showing the processing procedure of a test preprocessing method according to the embodiment.

The test preprocessing method according to this embodiment will be described below with reference to the procedures of FIGS. 4 and 5.

As preprocessing, the transfer mechanism 19 holds the test tube 25 moving along the conveyance path 20a and sets it at the image capture point P1 in the chamber 45. Note that the lid 26 is opened/closed at a predetermined timing to put or take the test tube 25 in or out of the chamber 45. At the time of image capture, the lid is closed to prevent external light from entering.

First, in Act1, the control unit 18 controls the image acquisition unit 14 to perform front light image capture as first image capture processing. As shown in FIG. 6, at the time of front light image capture (first image capture), the front light 42 irradiates the specimen container 25 with light from the image capture front surface side and captures the specimen container 25 in the upright state from the front surface side, thereby acquiring front image information.

The control unit 18 causes the storage unit 16 to store the image acquired in Act1 as a first image.

Next, the control unit 18 causes the data processing unit 17 to perform identification information reading processing (Act3). As shown in FIG. 7, the data processing unit 17 performs image processing based on the first image information acquired by front light image capture so as to detect identification information represented by the bar code 27a.

In addition, the data processing unit 17 performs image processing based on the first image information so as to detect the specimen size. As the specimen size, for example, a tube length L1 and a tube diameter D1 of the test tube 25 are detected (Act4).

Figure 9:
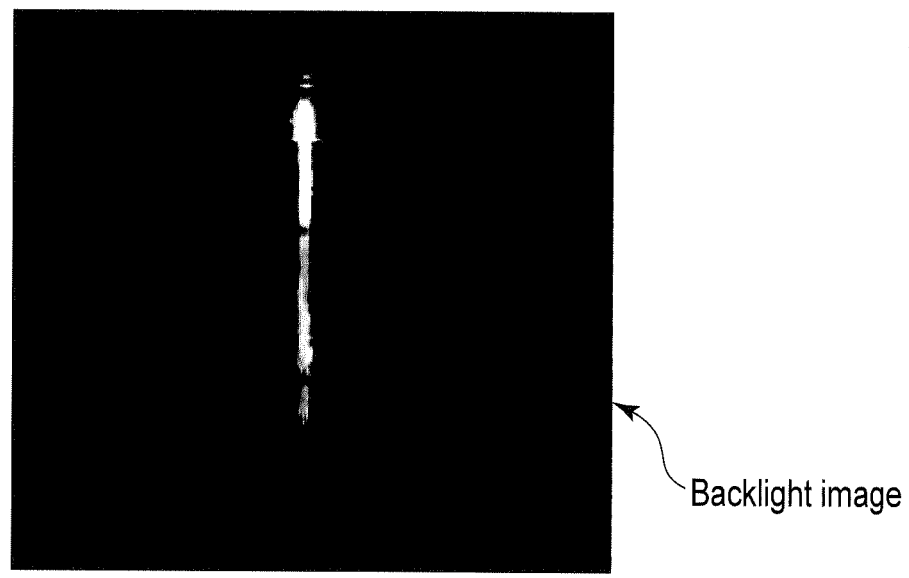
FIG. 9 is a photo showing a backlight image in the test inhibiting factor detection step.

Next, the control unit 18 controls the image acquisition unit 14 to perform backlight image capture as second image capture processing for region specification (Act5). In this backlight image capture, the backlight 43 irradiates the test tube with light from the rear surface side, and the light that has passed through the specimen 25a and the test tube 25 is received to capture an image under a light amount and shutter speed preset for boundary specification. Note that to specify the boundaries by one-time image capture, the image capture for boundary specification is performed by setting a relatively large light amount in consideration of light transmission through the specimen 25a. In the image acquired by the backlight image capture processing, for example, only the exposed portion 27b that passes the light is bright, and the other portions are dark, as shown in FIG. 9.

Figure 10:
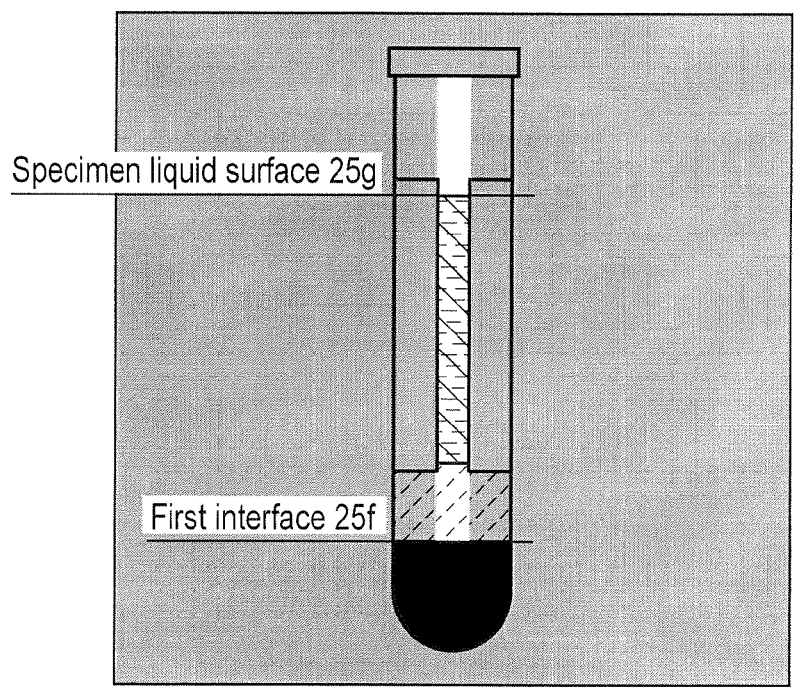
FIG. 10 is an explanatory view showing position detection processing of the test inhibiting factor detection step.
Figure 11:
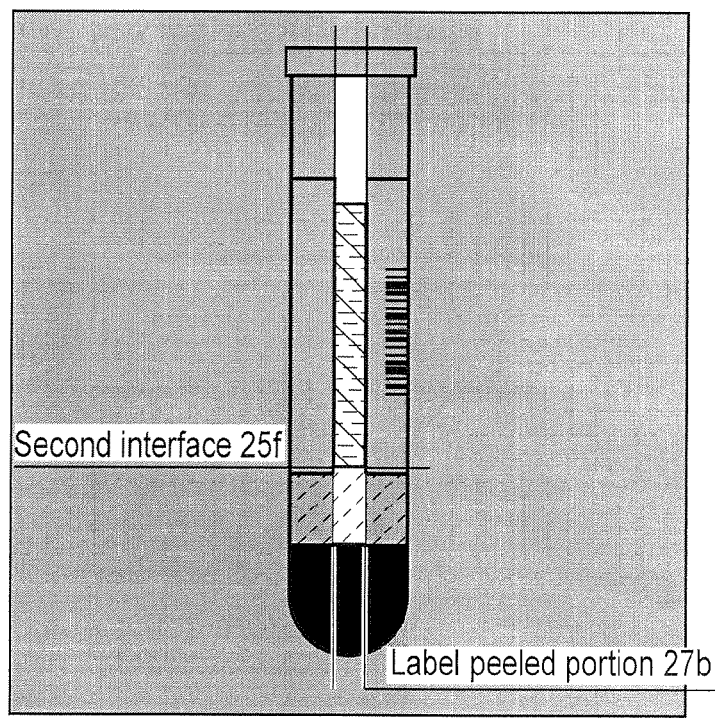
FIG. 11 is an explanatory view showing position detection processing of the test inhibiting factor detection step.

The control unit 18 performs boundary position detection processing by image processing based on the second image information (Act6). The data processing unit 17 detects the liquid level position of the specimen liquid surface 25g and the liquid level position of the first interface 25e, as shown in FIG. 10. Additionally, as shown in FIG. 11, the data processing unit 17 detects the liquid level position of the second interface 25f and the position and width of the exposed portion 27b of the label 27 by image processing (image analysis).

The control unit 18 specifies a determination target region AR based on the various kinds of information obtained in Act6 (Act7). That is, since a portion of the exposed portions 27b sandwiched between the liquid level position of the specimen liquid surface 25g and the liquid level position of the second interface 25f is the blood serum portion of the determination target, as shown in FIG. 10, this portion is detected as the determination target region AR.

Next, the control unit 18 controls the image acquisition unit 14 to perform backlight image capture (third image capture) for inhibitor detection (Act8). In this backlight image capture, the backlight 43 irradiates the test tube with light from the rear surface side, and the light that has passed through the specimen 25a and the test tube 25 is received to capture an image under a preset initial light amount. In the image acquired by the backlight image capture processing, for example, only the exposed portion 27b that passes the light is bright, and the other portions are dark, as shown in FIG. 9.

The brightness of the image of the specimen 25a is detected by image processing using the HSV method based on the image information. The detected brightness is compared with a preset brightness (Act9). If the detected brightness is lower than the set brightness (NO in Act9), the shutter speed is adjusted to be lower, and image capture is performed again (Act10). The image capture is repetitively performed a plurality of number of times until the preset brightness is reached. For example, image capture is performed first at a reference shutter speed (light amount), and the brightness is detected by image processing using the HSV method based on the acquired image information. It is determined whether the detected brightness is equal to or higher than the preset brightness. When the brightness of image information acquired by the image capture unit 41 has reached the preset brightness (YES in Act9), the image capture ends.

The control unit 18 causes the storage unit 16 to store the shutter speed at which the set brightness has been reached (Act11). The control unit 18 also causes the storage unit 16 to store the image information of a portion of the image acquired by image capture at the set brightness, which corresponds to the target region AR specified in Act7, as the target image of third image information to be used for various kinds of determination processing to be described later (Act12).

Next, test inhibiting factor detection processing of detecting test inhibiting factors such as the presence of a fibrin inclusion and defective blood clotting as well as chylous, hemolytic, and icteric states from the third image information by image processing is performed (Act13).

The processing steps of the test inhibiting factor detection processing will be explained with reference to FIG. 5. First, the data processing unit 17 performs chyle predetermination from the shutter speed information stored in Act11 (Act21).

"Chyle" is a state in which a fat has fragmented to make the specimen whitish or the specimen has absorbed a fat and has become whitish. The chyle may make it impossible to accurately measure some blood test items. In this embodiment, determination by the HSV method is performed using the whitish characteristic of the chyle.

Note that as a characteristic feature, a hue value by the HSV method generally hardly varies even if the light amount changes. On the other hand, RGB color components by the RGB method largely vary when the light amount changes. Hence, when the HSV method is used to determine the chylous and hemolytic states, a hemolytic state can accurately be detected.

As described above, in Act8 to Act11, the shutter speed is adjusted based on the brightness detected by the HSV method as part of chyle predetermination. When the light transmitted through the specimen upon backlight image capture has reached the predetermined set brightness, the value of the shutter speed corresponds to the light transmittance of the specimen 25a. Hence, in the chyle predetermination, the degree of chyle is primarily determined from the shutter speed. The lower the shutter speed is, the stronger the chylous state of the specimen is determined to be. The chyle predetermination is thus performed. For example, comparison with a plurality of preset thresholds is performed to determine the chyle level on a plurality of scale steps.

Primary hemolysis determination is performed from the chyle predetermination result and the third image information (Act22). "Hemolysis" is a phenomenon that red blood cells rupture, and hemoglobin is released out of them. At this time, other components of the red blood cells are also released and affect the test values and the like. In this embodiment, the hemolytic state is determined using the characteristic of hemolysis that changes the blood serum color to red. As the hemolysis predetermination, the data processing unit 17 performs image processing based on the third image information that is the backlight image adjusted to a predetermined brightness and detects the hue value (0 to 255) of the determination target region AR by the HSV method.

In the HSV method, the hue value may return to 255 because it is represented by a hue circle. In this case, 255 is subtracted to set the hue value to 0. Note that the shutter speed is adjusted such that the third image information has a predetermined brightness. In this embodiment, the color difference caused by hemolysis is determined by H (hue) of the HSV method, which is hardly affected by a change in the light amount, using the image information captured under a predetermined brightness obtained by adjusting the shutter speed, thereby stably extracting the color component.

When the hue changes due to the influence of chylous component inclusion, and for example, the chyle level is high, the color of the specimen 25a is affected to be reddish. Hence, as hemolysis determination (secondary determination), correction processing is performed based on the chyle predetermination result based on the hue value of hemolysis predetermination (Act23). That is, if the chyle level is high, and the shutter speed is low based on the chyle predetermination result, correction processing is performed to make the hue value detected in Act22 slightly higher and lower the hemolysis level. The hemolysis determination result based on the corrected hue value is obtained as the final hemolytic state determination result.

On the other hand, the turbid state changes depending on the content of hemolytic components. Hence, in this embodiment, chyle determination (secondary determination) is performed by correcting the chyle predetermination result based on the degree of hemolysis. As the chyle determination, correction processing is performed to subtract the influence of the degree of hemolysis on the brightness (Act24). That is, if the content of hemolysis components is high based on the result of hemolysis determination (Act23), the light hardly passes through. Hence, correction processing is performed to make the shutter speed higher than that determined based on the image capture result in Act8 (shorten the shutter open time) and lower the chyle level. Note that the correction amounts in Act23 and Act24 are set in advance in consideration of the mutual influence of chyle and hemolysis. The chyle determination result based on the corrected shutter speed is obtained as the final chylous state determination result.

Next, an icteric state is detected. "Icterus" is a state in which the amount of bilirubin in blood increases, and the tissues of skin, mucosae, and the like are stained yellow. In blood serum, the yellowness tends to deepen due to the increase in the bilirubin amount.

In this embodiment, the determination is done using the tendency of the green component out of the color components of a blood serum specimen to be stronger as the icterus level rises. Note that the red component or green component becomes stronger in the icteric state. Since the color components overlap those of hemolysis and chyle, it is difficult to perform the determination using only the hue.

Analysis of icteric specimen data has revealed that the green component is stronger and the blue component is weaker in the icteric specimen than in a normal specimen. In this embodiment, the RGB method is employed to detect the icteric state in consideration of the above-described fact.

Note that in this embodiment, since the light amount is adjusted to a predetermined amount in advance in Act8 for the third image information, variations in parameters can be prevented.

In chyle, the green component tends to be strong. Hence, if the determination is done based on only the green component, the determination value of chyle may conflict with that of icterus. If the determination is done based on only the blue component, the determination value of hemolysis may conflict with that of an icteric state. Considering these facts, the presence/absence of icterus is determined first based on the G/B value, and the degree of icterus is determined next based on the G value in this embodiment.

First, the control unit 18 causes the data processing unit 17 to determine the presence/absence of icterus as primary icterus determination based on the third image information (Act25). When determining the presence/absence of icterus, first, the color components of the determination target region are extracted based on the third image information by image processing using the RGB method. The presence/absence of icterus is determined based on the ratio of the green and blue components (G/B value) out of the extracted RGB components.

If the icterus value is equal to or larger than a predetermined threshold, it is determined that icterus exists. On the other hand, if the icterus value is smaller than the threshold, it is determined that icterus does not exist. The threshold of the icterus value is, for example, G/B=7.0.

Upon determining in Act25 that icterus exists, the degree of icterus is determined as secondary icterus determination (Act26). The determination of the degree of icterus is done based on the absolute value of green (green value) of the color components extracted by the RGB method in Act25. For example, the larger the G value is, the higher the icterus level is determined to be.

It is determined next whether the determination target region AR contains fibrin, defective blood clotting, and the like (test inhibiting factors) that are not present in normal blood serum (Act27).

FIG. 13 shows an internal sectional view <a> and a state <b> viewed from the outside of a container with a specimen containing fibrin. "Fibrin" is the end product of blood coagulation or a paste-like lump of protein fiber (fibrinogen). In a blood test, red blood cells+fibrin are separated by centrifugation to obtain blood serum as a supernatant. However, if coagulation delays as compared to usual, fibrin precipitation may be incomplete at the time of centrifugation, and precipitation may continue even after separation of the blood serum. In this case, an agar-like semisolid is formed in the blood serum to impede automatic dispensing. Fibrin is visually recognizable or unrecognizable and has various shapes. Fibrin is a semitransparent substance floating in the blood serum. When fibrin exists, the blood serum in the determination target region has a density difference.

FIG. 14 shows an internal sectional view <a> and a state <b> viewed from the outside of container with a specimen with defective blood clotting. "Defective blood clotting" is a state in which formation of the separating medium layer fails between the blood serum (blood serum/blood plasma) layer and the blood clot (blood clot/blood cell) layer due to insufficient movement of the separating medium after the centrifugation so that the layers are not completely separated. In this case, automatic dispensing is impeded, as in fibrin precipitation.

In these test inhibiting factor present states, the density in the blood serum layer is not even. For this reason, in Act27, as test inhibiting factor present state determination processing, the density difference in the determination target region AR is detected by image analysis based on the third image information, and it is determined based on the density difference whether the blood serum layer is even. If the blood serum layer is not even, it is determined that the blood serum layer has a test inhibiting factor.

The data processing unit 17 performs general final determination based on the results of various test inhibiting factor determinations performed in Act21 to Act27 (Act28). In the general final determination, for example, based on the result of chyle determination, the result of hemolysis predetermination, the result of icterus presence/absence and icterus degree determination, and the result of test inhibiting factor inclusion determination, if the level of each item is equal to or higher than a predetermined level, the specimen is determined to be untestable. If the level is lower than the predetermined level, the specimen is determined to be testable. If the level falls within a predetermined range, the specimen is determined to be testable, but the test result needs to be corrected.

According to the test preprocessing apparatus 10 of this embodiment, the following effects are obtained. That is, since the chylous state or hemolytic state is determined using the HSV method hardly affected by the light amount, the determination can be done accurately.

As the second image capture processing, the brightness of the third image information is adjusted in advance by changing the shutter speed for the backlight and kept at a predetermined brightness. This allows to accurately perform image processing (image analysis) later. In addition, correction processing is performed for the chylous state and the hemolytic state which readily affect each other's determination results. This enables more accurate determination.

Since the chylous state and the hemolytic state are detected by the HSV method, and the icteric state is detected by the RGB method from common image data maintained at a predetermined brightness, the detection accuracy can be improved. In the icteric state determination, the presence/absence of icterus is determined based on the G/B value using the RGB method. This makes it possible to distinguish a normal specimen from a specimen in the chylous or hemolytic state. It is possible to prevent the determination values from conflicting with each other and thus perform accurate detection.

Furthermore, in this embodiment, the third image information obtained by the backlight image capture under a predetermined brightness is commonly used for a plurality of types of determinations. It is therefore possible to quickly and accurately determine a plurality of types of test inhibiting factors.

[Second Embodiment]

Figure 15:
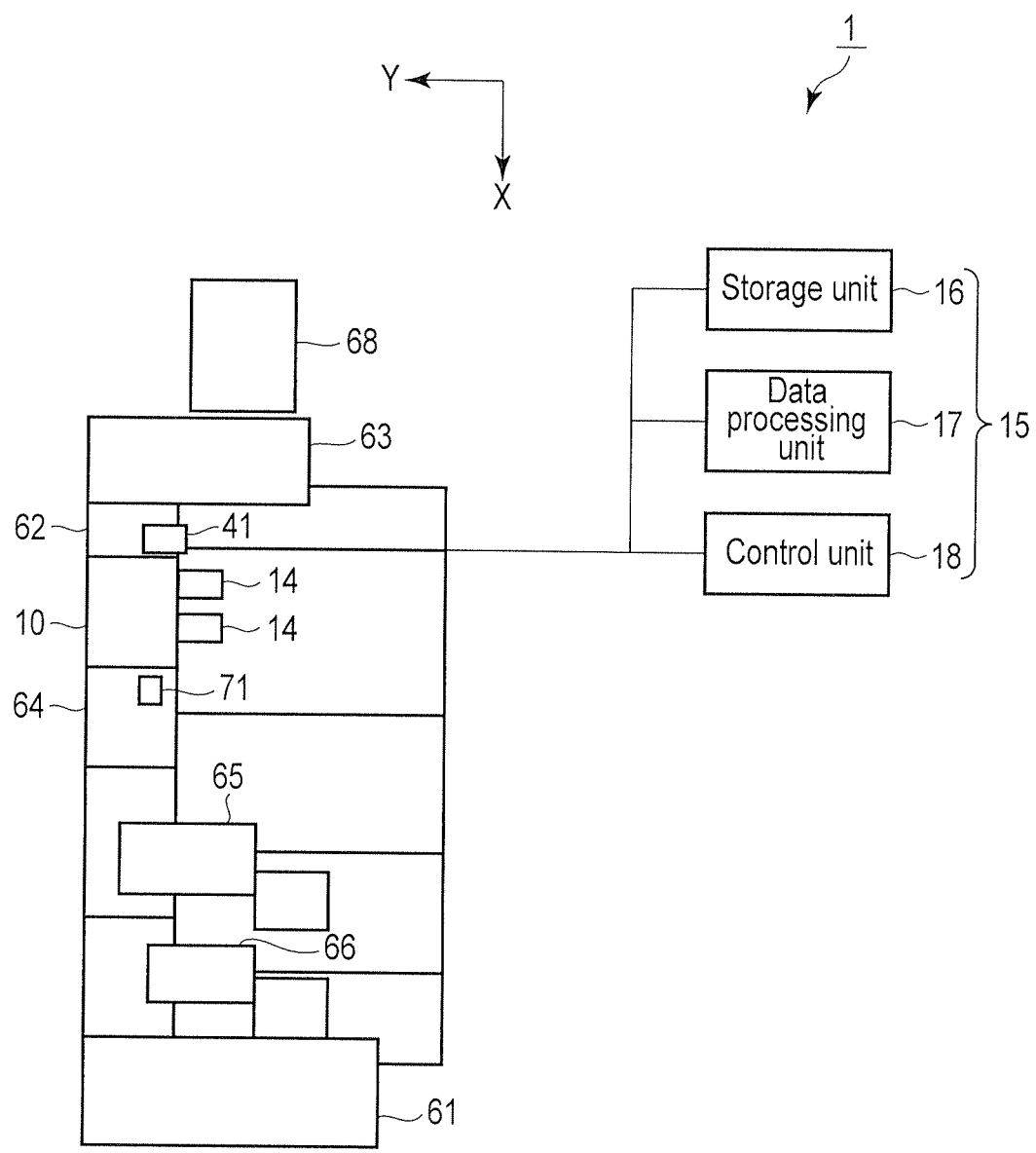
FIG. 15 is an explanatory view showing the arrangement of an analysis apparatus according to another embodiment.

An analysis apparatus 1 serving as a specimen processing apparatus according to the second embodiment of the present invention will be described below with reference to FIG. 15. FIG. 15 is a plan view schematically showing the analysis apparatus 1 including a test preprocessing apparatus 10. The analysis apparatus is constituted by juxtaposing a plurality of apparatuses individually constituted so that their conveyance paths continue.

The analysis apparatus 1 is constructed by arranging a loading device 63, a label peeling device 62, the test preprocessing apparatus 10, a sorting device (sorting means) 64, an unloading device 65, a batch dispensing device (batch dispensing means) 66, and an analysis device 61 in the order of processing from the upstream side to the downstream side of a predetermined conveyance path. Each device is provided with a conveyor-type conveyance unit that conveys a test tube 25 and arranged such that the conveyance paths of the plurality of conveyance units continue.

The loading device 63 comprises a conveyance unit that conveys a holder 24 along the conveyance path, and a transfer mechanism such as a robot arm. The loading device 63 transfers the test tube 25 in a rack installation unit 68 provided on, for example, a side onto the conveyance path.

The label peeling device 62 comprises a shaving mechanism 41 provided on a side of the conveyance path. The shaving mechanism 41 peels a label 27 to form an exposed portion 27b. The shaving mechanism 41 includes a pair of cutters on the front and rear sides which can, for example, move in the vertical direction. The shaving mechanism 41 vertically shaves off the label 27 bonded to the outer peripheral surface of the test tube 25 moving on the conveyance path, thereby forming the pair of exposed portions 27b on the front and rear sides each having predetermined width.

The test preprocessing apparatus 10 is constituted as in the first embodiment. The test preprocessing apparatus 10 performs the processing steps of Act1 to Act28, as in the first embodiment, so as to perform various kinds of test inhibiting factor detection processing by image processing based on image information captured from a side of the test tube 25.

The sorting device 64 comprises a conveyance unit that conveys the holder 24, and a gate portion 71 serving as a guide means for guiding the conveyance direction of the holder 24 based on the test inhibiting factor detection result under the control of a control unit 18.

A branch portion is provided at the midpoint of the conveyance path. There is provided a branch path that branches from the conveyance path and forms a different path. The gate portion 71 performs a switching operation to distribute the test tube 25 determined to be untestable to the branch path under the control of the control unit 18. For example, the test tube 25 that stores a specimen 25a determined to be untestable due to a test inhibiting factor is guided to the branch path. The normal test tube 25 is guided to be fed to the batch dispensing device 66 on the downstream side along the conveyance path. The downstream side of the branch path continues to the unloading device 65 that performs a step different from that of a normal specimen for a specimen in the chylous or hemolytic state. On the other hand, a normal specimen that is neither in the chylous state nor in the hemolytic state is guided to the batch dispensing device 66 on the downstream side along the conveyance path.

The unloading device 65 unloads the test tube 25 that stores the specimen 25a determined to be untestable because of, for example, a test inhibiting factor and excludes it from the batch dispensing target.

The batch dispensing device 66 comprises a conveyance unit that conveys the holder 24 along the conveyance path 20a, and a batch dispensing chip capable of moving up and down and arranged to face the opening of the test tube 25. When the test tube 25 with the specimen is arranged and stopped at a predetermined position on the conveyance path, the batch dispensing chip measures a predetermined amount of blood serum from the test tube 25 with the specimen and dispenses the measured blood serum into a sample cup separately fed. The sample cup in which the blood serum has been dispensed is loaded into the analysis device 61 on the downstream side so as to undergo analysis processing.

Figure 16:
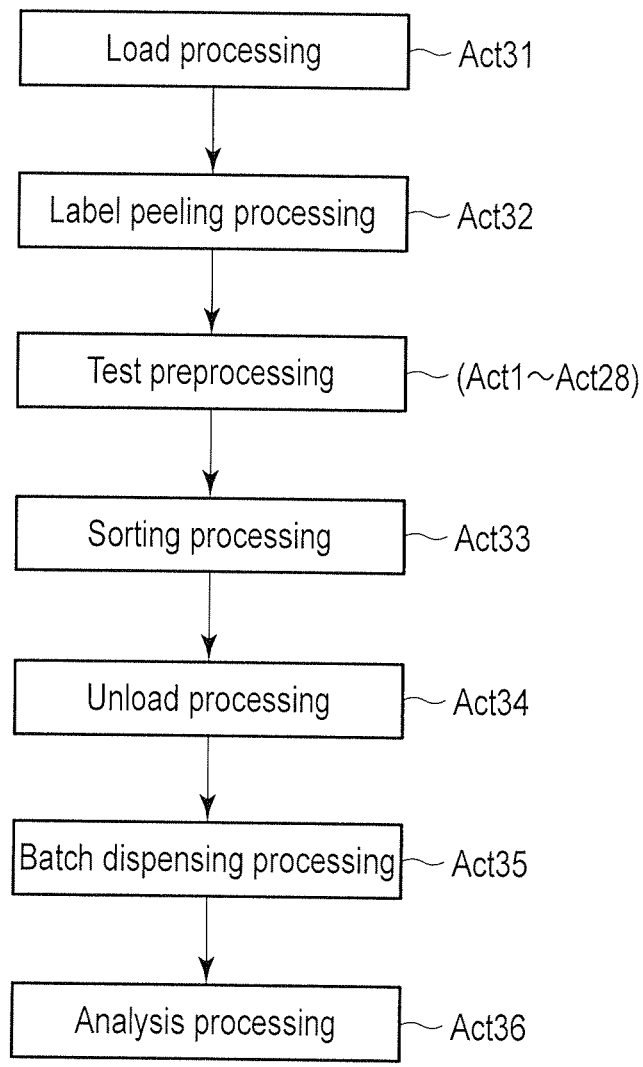
FIG. 16 is a flowchart for explaining steps in processing of the analysis apparatus.

The processing procedure of the analysis apparatus 1 will be described next with reference to FIG. 16. FIG. 16 shows the procedure of processing of the analysis apparatus 1. First, load processing is performed by causing the loading device 63 provided on the upstream side to grip the test tube 25 with the specimen stored in a test tube rack 68a and transfer it onto the conveyance path (Act31). The holder 24 stands by on the conveyance path. The test tube 25 is set in the holder 24. The transferred test tube 25 is fed to the label peeling device 62 while being held in the holder 24.

For the test tube 25 on the conveyance path, whose outer peripheral surface is covered with the label 27 without the exposed portions 27b necessary for image capture, the label peeling device 62 peels part of the label 27 at necessary portions, thereby forming the exposed portions 27b (Act32). For example, a pair of shaving mechanisms 41 provided on the sides of the conveyance path partially shave the label 27 adhered to the outer peripheral surface of the test tube 25, thereby forming the pair of exposed portions 27b each having a predetermined width. The test tube 25 after label peeling is fed to the test preprocessing apparatus 10 on the downstream side along the conveyance path.

The test preprocessing apparatus 10 performs the processing of Act1 to Act28, as in the first embodiment. The test tube 25 that has undergone test inhibiting factor detection processing is fed to the sorting device 64 on the downstream side while being held upright in the holder 24.

The sorting device 64 provided on the downstream side of the test preprocessing apparatus 10 switches the gate portion 71 in accordance with the general determination result in Act28 so as to distribute the test tube 25 under the control of the control unit 18 (Act33). For example, the test tube 25 storing the specimen 25a determined to be untestable is guided to the branch path and thus guided to the unloading device 65 on the downstream side by switching the gate portion 71. On the other hand, a normal specimen that is neither in the chylous state nor in the hemolytic state is guided to the batch dispensing device 66 on the downstream side along the conveyance path.

The unloading device 65 on the downstream side of the branch path unloads the test tube 25 that stores the specimen 25a determined to be untestable because of a test inhibiting factor and excludes it from the batch dispensing target (Act34).

In the batch dispensing device 66, batch dispensing processing is performed by causing the batch dispensing chip to measure a predetermined amount of blood serum from the test tube 25 with the normal specimen and dispense it into a sample cup separately fed (Act35). The sample cup in which the blood serum has been dispensed is unloaded from the unloading device on the downstream side and loaded into the analysis device 61 via the downstream connection path. The analysis device 61 performs analysis processing of testing various kinds of reactions (Act36).

According to the analysis apparatus 1 of this embodiment, a test inhibiting factor is detected in advance by test preprocessing, thereby changing the reagent dilution ratio or test conditions in accordance with the test inhibiting factor before analysis processing or excluding the specimen from the test target. This allows to prevent waste of test processing or reagents. In addition, when image analysis is performed using an image common to a plurality of test inhibiting factors, detection can be performed quickly and accurately.

Note that the present invention is not exactly limited to the above embodiments, and constituent elements can be modified in the stage of practice without departing from the spirit and scope of the invention. For example, a case has been exemplified in the above embodiments in which specimen processing is performed for each test tube 25. However, the processing may be performed simultaneously for a plurality of test tubes 25.

In the above embodiments, a case has been described in which a plurality of test inhibiting factors including icterus and a test inhibiting factor present state as well as chyle and hemolysis are detected. Some items may be omitted, and other items may be added. In the above embodiments, image capture information obtained when a predetermined brightness has been set is commonly used. However, another image information may be captured anew and used as target image information.

In the above embodiments, an example has been described in which in the target test tube 25, the label 27 is peeled off in advance in a predetermined region to form the pair of exposed portions 27b. However, the present invention is not limited to this. For example, the label peeling device for peeling off the label 27 of the test tube 25 before image acquisition may be provided on the upstream side of the conveyance path or as a separate device so as to peel off a predetermined region necessary for image capture as preprocessing of image capture in case of the absence of the exposed portion 27b formed at a predetermined position. For example, if the label 27 covers the whole peripheral surface of the test tube 25, the label peeling device may peel off the label at a necessary portion. A mechanism for changing the direction of the test tube 25 may be provided to perform preprocessing of satisfying a condition to allow light transmission.

Each constituent element exemplified in the above embodiments may be omitted, and the shape, structure, and material, and the like of each constituent element may be changed. Various inventions can be formed by properly combining a plurality of constituent elements disclosed in the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A test preprocessing method comprising:
   detecting a brightness of a specimen based on image of the specimen acquired by capturing the image by backlight image capture by an image acquisition unit before test processing of the specimen, and detecting a chylous state of the specimen based on the brightness;
   controlling the image acquisition unit such that the image acquisition unit repetitively performs the backlight image capture while adjusting a shutter speed until the brightness of the image reaches a predetermined value;
   detecting the chylous state based on the shutter speed value in a state in which the brightness has reached the predetermined value;
   detecting a hue of the specimen based on the image captured at the shutter speed in the state in which the brightness has reached the predetermined value; and
   detecting a hemolytic state of the specimen based on the hue.

2. The method according to claim 1, comprising:
   detecting the brightness and the hue of the specimen by an HSV method;
   correcting the hue value obtained based on the hue and the brightness; and
   correcting the chylous state of the specimen based on a detection result of the hemolytic state.

3. The method according to claim 1, comprising detecting RGB color component information of the specimen by image processing based on the image, and detecting an icteric state of the specimen based on the color component information.

4. The method according to claim 1, comprising detecting density information of an image in a target region by image processing based on the image, and detecting a test inhibiting factor present state of the specimen based on the density information.

5. The method according to claim 1, comprising:
   acquiring front light image by capturing a specimen container storing the specimen while irradiating the specimen container with light from a front surface side;
   reading identification information added to the specimen container by image processing based on the front light image;
   detecting size information of the specimen container by image processing based on the front light image;

acquiring backlight image by capturing the specimen container while irradiating the specimen container with the light from a rear surface side;

detecting a liquid surface position of a liquid layer in the specimen container based on the backlight image;

detecting a determination target region in the backlight image based on the liquid surface position; and detecting the chylous state and the hemolytic state of the specimen based on the brightness and the hue in the determination target region of the backlight image obtained by capturing the specimen container irradiated with the light from the rear surface side.

6. A test preprocessing apparatus comprising:

an image acquisition unit configured to acquire an image by capturing an image before test processing of the specimen; and a specimen state detection unit configured to perform a test preprocessing method of claim 1.

7. A specimen processing apparatus comprising:

a test preprocessing apparatus of claim 6; and an analysis unit provided on a downstream side of a specimen state detection unit on a conveyance path and configured to perform analysis processing of analyzing the specimen by making the specimen react with a reagent.

8. The apparatus according to claim 7, comprising:

a batch dispensing unit provided on the downstream side of an image acquisition unit of the test preprocessing apparatus and on an upstream side of the analysis unit on the predetermined conveyance path and configured to measure a portion of the specimen in a specimen container and dispense the measured specimen into a sample cup; and a sorting unit provided on the downstream side of the image acquisition unit of the test preprocessing apparatus and on the upstream side of the batch dispensing unit on the predetermined conveyance path and configured to perform sorting processing of the specimen container in accordance with a result of specimen state detection.

* * * * *